United States Patent [19]

Bachynsky et al.

[11] Patent Number: 5,190,748
[45] Date of Patent: Mar. 2, 1993

[54] ABSORPTION ENHANCEMENT OF ANTIBIOTICS

[75] Inventors: Maria O. Bachynsky, Nutley; Martin H. Infeld, Upper Montclair; Navnit Shah, Clifton; Joel Unowsky, Livingston, all of N.J.

[73] Assignee: Hoffmann-La Roche Inc., Nutley, N.J.

[21] Appl. No.: 809,244

[22] Filed: Dec. 18, 1991

Related U.S. Application Data

[63] Continuation of Ser. No. 527,669, May 21, 1990, abandoned, which is a continuation of Ser. No. 274,590, Nov. 22, 1988, abandoned.

[51] Int. Cl.$^5$ .............................................. A61K 31/74
[52] U.S. Cl. ........................... 424/78.08; 424/78.24; 514/200; 514/201; 514/202; 514/535; 514/946; 514/947; 540/222; 540/225; 540/228
[58] Field of Search .................. 424/78, 80, DIG. 5, 424/78.08, 78.24; 514/946, 947, 200, 201, 202, 535; 540/222, 225, 228

[56] References Cited

U.S. PATENT DOCUMENTS

| | | | |
|---|---|---|---|
| 4,485,033 | 11/1984 | Kitao et al. | 252/315.4 |
| 4,525,339 | 6/1985 | Behl et al. | 424/462 |
| 4,722,941 | 2/1988 | Eckert et al. | 514/784 |
| 4,760,059 | 7/1988 | Behl et al. | 424/DIG. 5 |
| 4,837,025 | 6/1989 | Guillemet et al. | 424/448 |

FOREIGN PATENT DOCUMENTS

| | | | |
|---|---|---|---|
| 0024031 | 2/1981 | European Pat. Off. | |
| 0091502 | 10/1983 | European Pat. Off. | |
| 0126348 | 11/1984 | European Pat. Off. | |
| 0179583 | 4/1986 | European Pat. Off. | |
| 56-100712 | 8/1981 | Japan | |
| 56-104812 | 8/1981 | Japan | |
| 0011431 | 1/1985 | Japan | 514/946 |
| 2028655 | 3/1980 | United Kingdom | 514/206 |

OTHER PUBLICATIONS

*Organic Chemistry* 2nd ed. T. W. Graham Solomons p. 948 (Table 21.3).

*Primary Examiner*—Thurman K. Page
*Assistant Examiner*—Robert H. Harrison
*Attorney, Agent, or Firm*—George M. Gould; George W. Johnston

[57] ABSTRACT

The absorption of antibiotics given through oral and rectal routes of administration is significantly enhanced by use of the antibiotic in conjunction with a two-component absorption enhancing system made up of an ether of a $C_6$ to $C_{18}$ alcohol and a polyoxyethylene glycol together with a second component selected from among polyoxyethylene glycol $C_6$ to $C_{18}$ glyceride esters, $C_6$ to $C_{18}$ carboxylic acids or salts thereof, and esters of two or more $C_6$ to $C_{18}$ carboxylic acids, glycerol and a polyoxyethylene glycol. A carrier and adjuvants are usually included. These compositions can be administered in any convenient oral or rectal dosage form, including tablets, capsules, beadlets and suppositories.

21 Claims, No Drawings ns
ABSORPTION ENHANCEMENT OF ANTIBIOTICS

This application is a continuation of application Ser. No. 07/527,669, filed May 21, 1990, which is a continuation of Ser. No. 07/274,590, filed Nov. 22, 1988, now abandoned.

BACKGROUND OF THE INVENTION

Since the first penicillin compounds were used successfully to fight pathogenic organisms such as bacteria, several generations of new anti-infective agents have been developed. Some of these agents, such as ceftriaxone, streptomycin, gentamicin and cefazolin, are normally poorly absorbed through mucosal tissue into the bloodstream and are, therefore, of limited or no practical value when administered via any route other than parenteral to fight systemic bacterial infections. Administration of these difficult-to-absorb drugs is sometimes accomplished by infusion, but more typically by intravenous or intramuscular injections.

Some injectable antibiotics, such as ceftriaxone, can be administered once a day and are therefore more convenient to use. However, for the most part, injectable antibacterial drugs must be given more frequently than once daily to achieve greatest effectiveness, and such treatments often require the services of a doctor, nurse or trained technician on a continual basis. The experience of frequent injections can also be distressful or unnerving for some patients.

Efforts have been made to find materials which promote the absorption of antibiotics and other pharmaceuticals that normally are poorly absorbed through mucosal tissue, the objective being to enable the formulation of non-injectable dosage forms such as capsules, tablets, pills, suppositories, and so forth with such pharmaceuticals. Some substances, such as ionic surfactants, sodium lauryl sulfate and cnelating agents (e.g., EDTA) are known to be rather harmful to the mucosal membrane, although they have been reported to enhance the intestinal absorption of large molecules. On the other hand, as described in the patent literature, the enhanced rectal absorption of antibiotics is obtained by the use of promoters such as hydroxy aromatic acid salts, e.g., sodium salicylate and sodium homovanillate, U.S. Pat. No. 4,406,896 (Higuchi et al.); cholic acid, or its salt, together with a fatty acid glyceride (e.g. WITEPSOL, known in the trade as Witepsol H15) and a polyethylene alkyl ether, Japan patent publication No. 57158-719; cholic acid, or its salt, together with a fatty acid glyceride, Japan patent publication No. 5062-007; a fatty acid glyceride (e.g., Witepsol) together with a polyoxyethylene glycol (PEG)-fatty acid ester, U.S. Pat. No. 4,732,753 (Füller); and a bile acid in combination with a polyoxyethylene-fatty acid ester and a glycerol-fatty acid ester, U.S. Pat. No. 4,156,719 (Sezaki).

The absorption promotion of orally delivered antibiotics with the use of a cholic acid salt or taurocholic acid salt is described by Miyamoto et al., in J. Pharm. Sci. 72. 651–654 (1983).

U.S. Pat. No. 4,525,339 (Behl et al.) discloses active oral dosage forms of beta-lactam antibiotics using $C_2$–$C_{12}$ fatty acid mono-, di- or triglycerides as the absorption enhancer.

The permucosal absorption of various therapeutics, including antibiotics, is reported to be enhanced by the use of fatty acids and saturated or unsaturated fatty acid glycerides, in Swiss patent publication No. 634,749.

SUMMARY OF THE INVENTION

In brief, the discovery has now been made that drug levels sufficient to treat or prevent bacterial infections in a host can be achieved by use of a method which comprises administering to the host a prophylactic or therapeutic amount of a pharmaceutical composition comprising (a) an antibacterial compound and (b) an absorption enhancing amount of a two-component absorption enhancing system made up of a first component which is (1) an ether of a $C_6$ to $C_{18}$ alcohol and a polyoxyethylene glycol (PEG) and a second component selected from among (2)(i) a polyoxyethylene qlycol - $C_6$ to $C_{18}$ carboxylic acid qlyceride ester, (2)(ii) a $C_6$ to $C_{18}$ carboxylic acid or pharmaceutically acceptable salt thereof and (2)(iii) an ester of two or more $C_6$ to $C_{18}$ carboxylic acids, glycerol and a polyoxyethylene qlycol. Optionally a pharmaceutically inert carrier can also be included.

The term "polyoxyethylene qlycol-$C_6$ to $C_{18}$ carboxylic acid glyceride ester" as used in connection with this invention refers to those reaction products derived from the co-reaction of polyoxyethylene glycol (or polymerizable precursor thereof such as ethylene oxide) with a $C_6$–$C_{18}$ carboxylic acid and qlycerol or with a $C_6$–$C_{18}$ carboxylic acid glyceride or qlycerides. Resulting from such reactions are typically mixtures of a polyoxyethylene glycol-$C_6$ to $C_{18}$ carboxylic acid qlyceride ester (e.g. PEG-qlycerol-caprate PEG-glycerol caprylate or PEG-glycerol-caprylate/caprate), a polyoxyethylene glycol-$C_6$ to $C_{18}$ carboxylic acid ester (e.g., PEG-caprate, PEG-caprylate or PEG-caprylate/caprate), and a glyceryl-$C_6$ to $C_{18}$ carboxylic acid ester (e.g., glyceryl mono-, di- or tricaprylate, glyceryl mono-, di or tricaprate or glyceryl mono-, di- or tricaprylate/ caprate), as the principal components.

More specifically, it has now been discovered that the above-identified absorption enhancing system functions to increase the extent of absorption of antibacterial compounds through mucosal tissue and into the bloodstream. This invention thus promotes the absorption and, concomitantly, the bioavailability of antibacterial compounds which, when administered without the absorption enhancer by means other than parenteral, are only poorly absorbed or not absorbed to any appreciable degree. The preparation and use of a greater variety of dosage forms for such compounds are thus enabled. The invention also promotes the greater absorption and bioavailability of antibacterial compounds which are otherwise only moderately absorbed through mucosal tissue, thus enhancing the effectiveness of such therapeutic compounds also.

This invention encompasses the administration of the aforementioned pharmaceutical composition in virtually any dosage form suitable for oral or rectal administration. Embraced within its scope are oral and rectal types of pharmaceutical preparations containing effective amounts of an antibacterial compound and an absorption enhancing system in accordance with the present description, with or without an inert carrier and pharmaceutically acceptable adjuvants.

DETAILED DESCRIPTION OF THE INVENTION

The terms "antibacterial" and "antibiotic" are used interchangeably throughout this disclosure to refer to bactericidal or bacteriostatic compounds which have been metabolically derived from a microorganism, synthetically prepared by chemical means, or prepared by a combination of microbial and chemical procedures (semi-synthetic).

Contemplated for utilization in the practice of this invention is virtually any antibiotic substance which is useful for combatting a bacterial infection in a host, including those antibiotics which are only moderately absorbed upon non-injected or non-infused administration. However, this invention finds its greatest usefulness when employed to enhance the absorption and bioavailability of antibiotics which, for the most part, can be effectively administered only by injection or infusion due to non- or poor absorbability via other routes of administration.

Among the most preferred antibacterial compounds suitable for use as the therapeutic substance in the practice of this invention are beta-lactam antibiotics, particularly compounds having a beta-lactam ring as the central structure, that is, the structure

which can be substituted at various positions on the ring and/or fused with other ring systems which themselves can be substituted or unsubstituted. Exemplary of such beta-lactam antibiotics are penicillins, cephalosporins, penems, carbapenems and monocyclic beta-lactams.

Especially preferred beta-lactam antibiotics for use in this invention are compounds of the formula

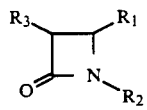

in which $R_1$ is hydrogen or optionally substitutes alkyl, $R_2$ is $SO_3\text{-}M+$ where $M+$ is a proton or cation, $R_3$ is an acylamino group or hydroxyalkyl, or $R_1$ and $R_2$ together with the beta-lactam (axetidinone) ring to which they are bonded represent

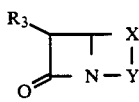

in which X is —S—, —O—, —SO—, —SO$_2$, —CH$_2$ or —CH(CH$_3$) and Y is group

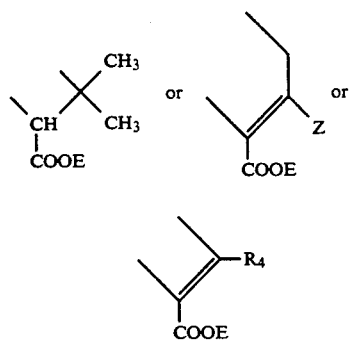

in which $R_4$ is a substituted thio group such as ethylthio, —SCH$_2$CH$_2$NH$_2$,

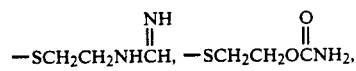

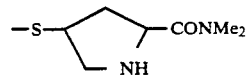

or an optionally substituted lower alkyl group such as aminomethyl, acylaminomethyl,

or a substituted oxy group such a carbamoyloxy

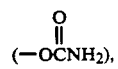

the carbon atom which carries the —COOE group is bonded to the nitrogen atom of the beta-lactam ring, Z is hydrogen, halogen, alkoxy or CH$_2$T, with T denoting hydrogen, alkyl —CO—O—, pyridinium, carboxamidopyridinium, aminopyridinium, carbamoyloxy, azido, cyano, hydroxyl, the group -S-phenyl which can be substituted or the group -S-het wherein "het" is an optionally substituted 5- or 6-membered heterocyclic ring, and E is hydrogen, a pharmaceutically acceptable ester group or a salt-forming cation.

Examples of the 5- or 6-membered heterocyclic rings encompassed within "het" above are the following:

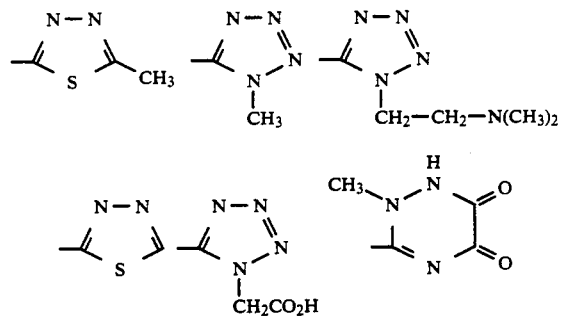

Especially preferred beta-lactam antibiotics and their pharmaceutically acceptable salts, esters and hydrates include ceftriaxone, a cephalosporin described in U.S. Pat. No. 4,327,210 (Montavon et al.); carumonam, a monocyclic beta-lactam described in European Patent No. EP 73061; piperacillin, a penicillin described in U.S. Pat. No. 4,112,090; cefamandole, a cephalosporin described in U.S. Pat. No. 3,641,021; mezlocillin, a penicillin described in U.S. Pat. No. 3,974,142; and cefazolin, a cephalosporin described in U.S. Pat. No. 3,516,997, the disclosures of all of which are incorporated herein by reference. Further included are cefoxitin, cefmetazole, cefotetan, moxalactam, cefuroxime, ceforamide, cefoperazone, ceftizoxime, cefotaxime, cefmenoxime, ceftazidime, cefsulodin, cefazolin, cephalexin, azlocillin, penicillin G, temocillin, sulbenicillin, ticarcillin, mecillinam, amoxicillin, methicillin, carbenicillin, thienamycin, N-formimidoylthienomycin, sulbactam and azthreonam.

Also included within the scope of this invention are antibiotics other than the beta-lactams, for example, vancomycin and gentamicin, the absorption and bioavailability of which are improved by use with the described absorption enhancing systems.

Absorption enhancing system component (b)(1) is the product of an etherification reaction between an alcohol, specifically, an acyclic $C_6$ to $C_{18}$ straight or branched chain alkanol and a polyoxyethylene glycol (PEG). Examples of alcohols suitable for the preparation of component (b)(1) include n-hexyl, n-heptyl, n-octyl, n-decyl, n-dodecyl (lauryl), n-tetradecyl (myristyl), n-hexadecyl (cetyl), n-octadecyl, and so forth. Lauryl alcohol is preferred.

The polyoxyethylene glycol is, typically, a medium to high molecular weight material which preferably has a number average molecular weight in the range from about 200 to about 1500, and more usually from about 400 to about 600.

Component (b)(1) can be prepared by known procedures.

Especially favored for use as component (b)(1) is the material known as Laureth-12 (CTFA designation). Laureth-12 is the polyethylene glycol ether of lauryl alcohol and has the formula:

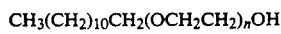

wherein n has an average value of 12. A suitable commercially available material is MACOL LA-12, manufactured by Mazer Chemicals Company, Gurnee, Ill.

Absorption enhancing system component (b)(2)(i), may be the product of an esterification reaction between a polyoxyethylene glycol, glycerol and one or more straight or branched chain $C_6$ to $C_{18}$ carboxylic acids, preferably a monofunctional acid or acids. Alternatively, component (b)(2)(i) may be prepared by oligomerizing or polymerizing ethylene oxide in the presence of an ester of glycerol and one or more of such $C_6$ to $C_{18}$ carboxylic acids (glyceride esters). Still another route, and the preferred one, is by co-reacting the glyceride ester or esters with a fully pre-formed polyoxyethylene glycol under conditions sufficient to achieve alcoholysis.

According to a particular preferred procedure, involving alcoholysis, a reaction vessel is charged with stoichiometric quantities of a glyceryl-fatty acid ester or esters and a polyethylene glycol. The vessel is closed and heated at atmospheric pressure to 200° C., with continuous stirring commenced at 70° C., for a period of 12 to 24 hours or until the reaction is completed. The vessel is allowed to cool and the reaction product is then separated from the reaction mixture by filtration.

Examples of $C_6$ to $C_{18}$ carboxylic acids, saturated or unsaturated, which are useful for the preparation of absorption enhancing system component (b)(2)(i) are caproic, caprylic, capric, lauric, myristic, oleic, palmitic and stearic. Especially preferred for this invention are capric and caprylic acids, individually or together.

The polyoxyethylene glycol (PEG) used in the formation of absorption enhancing system component (b)(2)(i) is, typically, a medium to high molecular weight material, preferably having a number average molecular weight in the range from about 200 to about 1500, and more preferably from about 300 to about 600.

A material which is suitable for use as absorption enhancing system component (b)(2)(i) will most preferably have the following characteristics:

Organoleptic Properties

Appearance: clear oily liquid
Odor: faint
Color: pale yellow to yellow

Physical and Chemical Properties

Acid Value: 0.2–0.6
Sulfated ash: less than 0.05%
Saponification index: 85–105
Iodine index: less than 2
Moisture content: less than 0.05%
Free glycerin content: approx. 2%
Monoglyceride content: approx. 6 to 8%
Density ($d_4^{20}$): 1.062–1.068 g/cc
Refractive index ($n_D^{20}$): 1.458–1.462

Suitable absorption enhancing system components for use in this invention which are commercially available are Labrasol, produced by Gattefosse Corporation, Paris, France (PEG-8 caprylate/caprate glyceride esters), and SOFTIGEN (known in the trade as Softigen 767), produced by Dynamit Nobel, West Germany (PEG-6 caprylate/caprate glyceride esters). Labrasol is known as polyethyleneglycol 400 caprylic/capric glycerides or polyoxyethylene(8) caprylic/capric glycerides. More particularly, it is an ethoxylated glyceride having the formula:

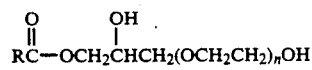

wherein RCO— is a mixture of caprylic and capric radicals, and n as an average value of 8.

The $C_6$ to $C_{18}$ carboxylic acid or its salt which constitutes absorption enhancing system component (b)(2)(ii) is derived from an acyclic carboxylic acid, which may be straight or branched chain. Examples include caproic, caprylic, capric, lauric, myristic, oleic, palmitic and stearic. Most favored for the purposes of this invention are caprylic and capric acids.

These salts can be prepared in a conventional manner and using known techniques by reacting the acid with a base having a non-toxic, pharmacologically and pharmaceutically acceptable cation. In general, any base which will form a salt with a carboxylic acid and the pharmacological properties of which will not cause an adverse physiological effect when ingested by or otherwise administered to a warm-blooded animal is suitable. Such bases thus include, for example, alkali metal and alkaline earth metal hydroxides or carbonates, such as sodium hydroxide, potassium hydroxide, calcium hydroxide, potassium carbonate, and the like. Particularly preferred for this invention are sodium salts, chiefly because of their ready availability.

Absorption enhancing system component (b)(2)(iii) is derived from a mixture of two or more carboxylic acids of 6 to 18 carbon atoms, glycerol and a polyoxyethylene glycol. The acids may be straight or branched chain, and saturated or unsaturated.

Suitable acids include saturated carboxylic acids such as n-hexyl, n-heptyl, n-octyl, n-decyl, lauryl, myristyl, cetyl and n-octadecyl, and unsaturated enoic (e.g., oleic) and dienoic (e.g., linoleic) acids.

Preferred are mixtures comprised of several $C_6$ to $C_{18}$ fatty acids, such as found in vegetable oils and fats, and most preferably coconut oil, which is composed of major amounts of saturated and minor amounts of unsaturated fatty acids of up to 18 carbon atoms.

Preferably, the polyoxyethylene glycol employed for absorption enhancing system component (b)(2)(iii) is characterized by a number average molecular weight in the range from about 200 to about 1500, and more usually from about 300 to about 600.

Absorption enhancing agents useful as absorption enhancing system component (b)(2)(iii) can be prepared by those skilled in the art using conventional esterification procedures. A suitable material is available commercially from Capital City Products, Janesville, Wis. under the trade designation ACCONO (known in the trade as Acconon Con) (a PEG glycerol cocoate).

The relative proportions of the two components which comprise the absorption enhancing system can be varied to achieve optimum results for a particular embodiment of the invention. Preferably, the weight ratio of (b)(1) to (b)(2)(i), (b)(2)(ii) or (b)(2)(iii) is in the range from about 1:50 to about 50:1, more preferably from about 1:10 to about 10:1, and most preferably from about 1:4 to about 4:1.

The effective amount of the absorption enhancing system, component (b), in the composition of this invention will vary depending on such factors as the particular antibacterial compound being employed and its amount, as well as the age of the subject being treated.

In general, for oral dosage form compositions of this invention, it is preferred to employ from about 50 to about 1000 milligrams (mg), and more preferably from about 100 to about 500 mg of the absorption enhancing system, for each unit dose of the composition. These compositions will usually contain the antibacterial compound in amounts from about 10 to about 500 mg, and more usually from about 50 to about 250 mg, per unit dose.

Rectal dosage form compositions in accordance with this invention will usually contain from about 50 to about 1500 mg, more preferably from about 75 to about 600 mg of the absorption enhancing system, for each unit dose of the composition. Such compositions will usually contain the antibacterial compound in amounts from about 10 to about 3000 mg, and more usually from about 100 to about 1500 mg, per unit dose.

The term "unit dose" is used here in the conventional sense to mean a single application or administration of the drug to the subject being treated in an amount as stated above, but it should be understood that the amount can be given in the form of a single pill, tablet, capsule, suppository, etc., or alternatively, in multiples of two or more of such dosage units with the total adding up to the stated amount of drug.

The described antibacterial compound and absorption enhancing system, components (a) and (b), respectively, can be incorporated into a vehicle, if desired. As the vehicle, there can be used any pharmaceutically acceptable solid, semi-solid or liquid carrier in which these components are soluble or readily dispersible. Some examples include but are not limited to cocoa butter, polyethylene glycols, polypropylene glycols, methylcellulose, carboxymethyl cellulose and suppocire semi-synthetic bases (Gattefosse Corp., Paris, France) SUPPOCIRE is a mixture of hydrogenated palm glycerides and palm kernal glycerides. Preferably, the vehicle is a solid. Favored as a solid vehicle for the compositions of this invention are mixtures of mono-, di- and triglycerides of $C_{12}$ to $C_{18}$ natural saturated fatty acids, preferably vegetable fatty acids having an even number of carbon atoms ($C_{12}$, $C_{14}$, $C_{16}$, etc.). Especially suitable and preferred are the pharmaceutical bases of Dynamit Nobel having the trade designation "WITEPSOL".

Still other pharmaceutically compatible carrier materials may be employed as desired and depending upon particular requirements, the selection of which is within the knowledge of those skilled in the art.

If utilized, the vehicle will generally be present in those amounts which are conventional for pharmaceutical carrier materials and which can be reasonably and safely administered.

The preferred method of orally administering the combination of antibacterial compound and absorption enhancing system in accordance with this invention is in the form of an enteric coated entity, and more specifically, an enteric coated solid dosage form. The formulation can be filled into a hard- or soft-shell capsule or, if the formulation is a liquid, absorbed onto a suitable carrier to make a free flowing powder and then filled into the capsule or, alternatively, compressed into a pill or tablet. Still other possible dosage forms include microcapsule or beadlet forms of the antibacterial compound mixed with the absorption enhancing system which may thereafter be encapsulated in an enteric coated capsule.

Usage of enteric coating materials in this manner serves to protect the antibacterial compound from the gastric fluid and to achieve optimum delivery of the antibacterial compound together with the absorption enhancing system to the intestine. The enteric coating material is, for the most part, resistant to the gastric fluid and is unaffected by it but dissolves in the intestinal fluid to cause release of the drug.

The effectiveness of particular enteric coating materials can be measured using known USP procedures. By way of illustration, suitable enteric coating materials for purposes of this invention include but are not limited to the following:

cellulose acetate phthalate
cellulose acetate trimellitate
hydroxypropyl methylcellulose phthalate
hydroxypropyl methylcellulose phthalate succinate
polyvinyl acetate phthalate
methacrylic acid
methacrylic acid esters These enteric coating materials may be applied with or without plasticizers, such as acetylated glycerides or diethylphthalate, using methods known to those skilled in the art.

The percentage of enteric coating applied is usually between about 1 and about 10 percent by weight, or more, and most desirably from about 2 to about 8 percent by weight, based on the total weight of the unit dosage form, i.e., the total capsule or table weight. Examples of suitable enteric coating formulations are given below.

| Enteric Coating Formulations | |
|---|---|
| Ingredients | % w/w |
| Preparation A: | |
| Hydroxypropyl methylcellulose phthalate (HPMCP) | 5.0 |
| Triacetin | 0.5 |
| Methylene chloride | 47.25 |
| Denatured alcohol | 47.25 |
| Preparation B: | |
| HPMCP | 10.0 |
| Titanium dioxide | 0.2 |

| Enteric Coating Formulations | |
| --- | --- |
| Ingredients | % w/w |
| Dimethyl polysiloxane | 0.05 |
| Acetone | 44.875 |
| Denatured alcohol | 44.875 |
| Preparation C: | |
| Cellulose acetate phthalate (CAP) | 8.5 |
| Diethyl phthalate | 1.5 |
| Titanium dioxide | 0.2 |
| Acetone | 44.9 |
| Denatured alcohol | 44.9 |
| Preparation D: | |
| Polyvinyl acetate phthalate | 5.0 |
| Acetylated glycerides | 0.8 |
| Methylene chloride | 47.1 |
| Denatured alcohol | 47.1 |
| Preparation E: | |
| Methacrylic acid or methacrylic acid ester (Eudragit S or L, Rohm Pharma, GMBH, Wetterstadt, West Germany) | 8.0 |
| Acetone | 46.0 |
| Anhydrous alcohol | 46.0 |
| Plasticizer | q.s. |

Oral dosage form compositions in accordance with this invention can also be formulated to additionally contain conventional additives or supplementary ingredients, in the usual amounts for such materials. By way of illustration, such additives or supplements include thickening agents, such as silicic acid (for instance, the trademark designating AEROSIL products); bentonites; colloidal clay; carboxymethyl celluloses; modified montmorillonites, such as alkyl ammonium salts of montmorillonites (for instance, the commercial products known as "BENTONE"); organic thickening and structure-forming agents, such as saturated higher fatty acids and alcohols containing from 12 to 20 carbon atoms (for instance, stearic or palmitic acids, or stearic or cetyl alcohols); waxes; monoglycerides of saturated or unsaturated high fatty acids such as stearic acid, palmitic acid or oleic acid; gelling agents, such as aluminum stearate; dispersing agents, such as ionic, non-ionic or cationic surfactants; emulsifying agents, such as lecithin, and so forth.

The compositions of this invention can also contain pharmaceutically acceptable adjuvants, such as binders or lubricants for tablettinq, stabilizing agents, antioxidants, flowing agents (to enhance pourability or flowability during processing), preservatives, flavoring agents, coloring agents and buffering agents. Any of these can be selected from among materials known for such purposes and used in conventional amounts.

In vivo tests were utilized to evaluate the enhanced mucosal tissue absorption of antibiotics administered in accordance with this invention.

IN VIVO (RATS)—ENTERAL

Adult Sprague-Dawley female rats (Charles River Breeding Laboratories, Kingston, N.Y.), weighing about 250 grams each, were fasted overnight and anesthetized with metofane. With each rat, an incision was made on the ventral surface to expose the intestine. Administration of an antibiotic was carried out using a solution dosage form. The solutions were prepared by dissolving 5 mg of antibiotic in water with or without absorption enhancer and diluting to the desired concentration.

Each solution of antibiotic in water was administered enterally by injecting with a syringe into the duodenum below the pyloric valve. For purposes of comparison the solution was alternatively administered intravenously by injecting with a syringe into a tail vein.

Plasma Levels of Antibiotic in Rats

The concentration of antibiotic in rat plasma was determined at various time intervals after intravenous or enteral administration. Blood samples were collected from the tail of each test animal prior to administration of the antibiotic and at 5, 10, 20, 40, 60, 120, 240 and 360 minutes after administration, then centrifuged at 3200 rpm for 5 to 10 minutes, after which the plasma was withdrawn and frozen until assayed.

Bioassay of Plasma Samples

Most of the antibiotics tested had exhibited some degree of protein binding when drug-spiked rat plasma was assayed against drug in $H_2O$. Any antibiotic not bound by plasma was diluted in $H_2O$ and assayed against standards prepared in $H_2O$. For bound antibiotics, the influence of protein binding was negated by diluting all standards and samples in pooled rat plasma. In the case of ceftriaxone and cefazolin, the effect of binding was accounted for by deproteinizing plasma samples with acetonitrile with a dilution factor of 1:12 and assaying against a standard curve diluted in $H_2O$. Antibiotic levels were assayed on nunc plates employing the appropriate agar seeded with bacteria, as listed below.

| Antibiotic | Assay Organism | Range of Standard Curves (mcg/ml) | Bioassay Media | Volume (mol) |
| --- | --- | --- | --- | --- |
| Carumonam | E. coil. 1346 | 32–1 | AA#1[2] | 20 |
| Ampicillin[1] | M. lutea ATCC 9341 | 8–0.25 | AA#1 | 20 |
| Cefamandole[1] | M. lutea ATCC 9341 | 32–1 | AA#1 | 20 |
| Cefotaxime[1] | E. coli. 1346 | 8–0.25 or 16–0.5 | AA#1 | 20 |
| Cefoxitin[1] | S. aureus MB2786 | 64–4 | BHI[3] | 20 |
| Ceftriaxone[1] | E. coil. 1346 | 4–0.125 | AA#1 | 20 |
| Cefazolin[1] | S. aureus ATCC 25923 | 32–1 | AA#1 | 50 |
|  | B. subtilis spores | 32–2 | AA#1 | 50 |
| Moxalactam[1] | E. coli 1346 | 50–1.56 | AA#1 | 50 |
| Penicillin G[1] | M. lutea ATCC 9341 | 8–0.5 | AA#1 | 20 |
| Mezlocillin[1] | M. lutea ATCC 9341 | 16–1 | AA#1 | 50 |
| Gentamicin[1] | K. pneumoniae A | 80–2.5 | MH[4] | 50 |

-continued

| Antibiotic | Assay Organism | Range of Standard Curves (mcg/ml) | Bioassay Media | Volume (mol) |
|---|---|---|---|---|
| Vancomycin[1] | B. cereus ATCC 11778 | 64-2 | AA#8[5] | 50 |

[1] Antibiotics protein bound in rat plasma.
[2] AA#1 = antibiotic agar #1 (Difco).
[3] BHI = Brain Heart Infusion Media (Difco).
[4] MH = Mueller Hinton Agar (Difco).
[5] AA#8 = antibiotic agar #8 (Difco).
mcg/ml = micrograms per milliliter
mcl = microliters The plates were incubated overnight at 37° C. and the zones of inhibition were read to the nearest 0.1 mm. Calculations were made using an autoassay machine (Giles Scientific, Inc., New York). For reference, see J.V. Bennett et al., Applied Microbiology 14, 170–177 (1966).

The results were as follows:

TABLE 1

ENTERAL ABSORPTION IN RATS -
With and Without Absorption Enhancers
Dose = 5 mg/0.5 ml

| | Cmax (micrograms per milliliter) | | | |
|---|---|---|---|---|
| Antibiotic | (Control) Water | Acconon Con + Laureth-12* | Labrasol + Laureth-12* | Sodium Caprylate (30%) + Laureth-12* |
| Carumonam | 0.0 ± 0.0 | 7.2 ± 1.4 | 11.7 ± 3.8 | 6.3 ± 2.4 |
| Cefamandole | 1.3 ± 2.5 | 6.4 ± 0.6 | 8.4 ± 2.6 | 18.1 ± 3.7 |
| Cefazolin | 0.0 ± 0.0 | 42.9 ± 3.0 | 62.2 ± 25.2 | 40.7 ± 7.2 |
| Cefoxitin | 0.0 ± 0.0 | 7.7 ± 2.8 | 9.1 ± 3.4 | 16.2 ± 4.6 |
| Cefotetan | 0.0 ± 0.0 | 9.5 ± 2.8 | 21.2 ± 5.8 | 26.1 ± 11.4 |
| Gentamicin | 3.9 | 15.4 ± 2.3 | 9.6 ± 1.9 | 14.1 ± 6.9 |
| Mezlocillin | 0.0 ± 0.0 | 0.6 ± 1.0 | 1.4 ± 1.4 | 6.7 ± 1.7 |
| Moxalactam | 0.0 ± 0.0 | 9.6 ± 2.2 | 16.2 ± 1.8 | 19.9 ± 4.5 |
| Penicillin G | 0.5 ± 0.1 | 3.5 ± 1.0 | 5.2 ± 1.6 | 7.4 ± 2.4 |
| Vancomycin | 2.9 ± 0.6 | 0.0 ± 0.0 | 6.9 ± 1.0 | 9.8 ± 3.5 |
| Ceftriaxone | 2.4 ± 1.9 | 38.8 ± 22.6 | 105.5 ± 23.0 | 53.7 ± 13.3 |

*Weight Ratio of Other Absorption Enhancer Component to Laureth-12 was 8:1

IN VIVO (DOGS) - ENTERAL

Six male beagle dogs, weighing about 10 to 16 kilograms each, were chronically fitted with a modified Thomas cannula implanted in the distal duodenum. Each dog received 2 hard shell gelatin capsules containing 210 mg of ceftriaxone sodium salt in 280 mg of a base (WITEPSOL H15), with absorption enhancer (157.5 mg of Labrasol and 52.5 mg of Laureth-12). Administration of the capsules in each instance was enteral through the modified Thomas cannula into the proximal jejunum. Drug dosage was 20 to 50 mg of ceftriaxone per kilogram of dog body weight.

Blood plasma concentrations of ceftriaxone were determined prior to administration and at 10, 20, 40, 60, 120, 180 and 240 minutes after administration. Measurements were made by withdrawing blood at these time intervals, centrifuging, separating the plasma and assaying by High Performance Liquid Chromatography (HPLC), reverse phase method, or by bioassay (the same procedure as previously described for the Bioassay of Plasma Samples).

To establish a standard curve, ceftriaxone was diluted with normal dog plasma, then deproteinized in the same manner as described previously. Calculations were conducted using a Waters 840 Computer System. Through the use of an appropriate computer program, the area under the curve (AUC) was determined for each route of administration. From these determinations, the bioavailability was computed using the following equation:

$$\% \text{ Bioavailability} = \frac{[AUC \text{ Enteral}]}{[AUC \text{ I.V.}]} \times 100$$

Whenever intravenous (I.V.) data were not available for the same dose level used enterally, the following equation was employed:

$$\% \text{ Bioavailability} = \frac{[AUC \text{ Enteral}]}{[AUC \text{ I.V.}]} \times \frac{[\text{I.V. Dose}]}{[\text{Enteral Dose}]} \times 100$$

The results were 45.4±18.2% Bioavailability and 19.5±6.5 mcg/ml Cmax for the absorption enhanced formulation, compared to 0% Bioavailability and 0.5 mcg/ml Cmax for the control (a solution of ceftriaxone in water equivalent to 25 mg/kg, no absorption enhancers).

IN VIVO (BABOONS)—ORAL

Adult baboons (Papio anubis and Papio hamadryas), ranging in weight from 12 to 30 kilograms, were used in this study. The baboons were fasted overnight, then sedated with ketamine hydrochloride by intramuscular injection prior to administration of the antibiotic. Each baboon received four hard shell gelatin capsules through a gastric tube. Each capsule contained the following:

| | |
|---|---|
| Ceftriaxone sodium salt | 300 mg |
| Labrasol | 225 mg |
| Laureth-12 | 75 mg |
| Witepsol H15 | 380 mg |
| | 980 mg |

Enteric coating: polyvinyl acetate phthalate (approximately 8% of total capsule weight)

One-milliliter blood samples were taken from the femoral region of each baboon using a heparinized 3-ml syringe. Samples were taken prior to ceftriaxone administration and at 15, 30, 60, 120, 240, 360, 480, 600 and 720 minutes following ceftriaxone administration. The samples were centrifuged at 12,000 rpm for one minute and the plasma was separated and bioassayed for antibiotic content after deproteinization with acetonitrile, using the same procedure described previously for the Bioassay of Plasma Samples.

The results were 10.0±6.5% Bioavailability and 5.5–59.8 mcg/ml Cmax range, compared to 0% Bioavailability and 0 mcg/ml Cmax for the control (ceftriaxone sodium salt, 300 mg, in the same enteric coated capsule, no absorption enhancers).

Absorption was also evaluated using a formulation composed of 300 mg of ceftriaxone sodium salt, 200 mg of sodium caprylate, 75 mg of Laureth-12 and 415 mg of Witepsol H15. The Bioavailability of this formulation was 15.7±9.9% and 15.0–66.3 mcg/ml Cmax range, compared to 0% Bioavailability and 0 mcg/ml Cmax for the control (same as above).

IN VIVO (DOGS)—ORAL

Male beagle dogs weighing approximately 10–14 kilograms were used in this study. The dogs received 2 or 3 hard shell capsules through a gastric tube. Each capsule contained the following:

| | |
|---|---|
| Ceftriaxone sodium salt | 300 mg |
| Labrasol | 225 mg |
| Laureth-12 | 75 mg |
| Witepsol H15 | 380 mg |
| | 980 mg |

Enteric coating: Polyvinyl acetate phthalate (approximately 8% of total capsule weight)

Blood plasma concentrations of ceftriaxone were determined prior to administration and at 10, 20, 40, 60, 120, 180 and 240 minutes after administration. Measurements were made by withdrawing blood at these time intervals, separating the plasma, deproteinizing, and assaying by High Performance Liquid Chromatography (HPLC), reverse phase method, or by the previously described Bioassay of Plasma Samples method.

The results were 34.2±14.0% Bioavailability and 21.6±7.6 mcg/ml Cmax for the above formulation, and 0% Bioavailability and 0 mcg/ml Cmax for the control (ceftriaxone sodium salt, 300 mg, in the same enteric coated capsule, no absorption enhancers).

Absorption was also evaluated using a formulation composed of 300 mg of ceftriaxone sodium salt, 200 mg of sodium caprylate, 75 mg of Laureth-12 and 415 mg of Witepsol H15. Bioavailability was 22.4±13.5% and Cmax was 14.4±8.4 mcg/ml, compared to 0% and 0 mcg/ml, respectively, for the control (same as above).

IN VIVO (BABOONS)—RECTAL

Male and female adult baboons (Papio anubis and Papio hamadryas), ranging in weight from 12 to 27 kilograms, were used in this study. The baboons were fasted for 24 hours prior to administration of antibiotic, then sedated with ketamine hydrochloride by intramuscular injection prior to administration of the antibiotic. Suppositories made up of the formulations shown below were administered to the baboons and the rectal openings were then taped closed to prevent expulsion and leakaqe of the suppository mass.

| | |
|---|---|
| Antibiotic | 500 mg |
| Laureth-12 | 125 mg |
| Labrasol | 250 mg |
| Witepsol H15 | 1125 mg |
| Total: | 2000 mg |

To measure antibiotic absorption into the bloodstream, blood samples were taken from the femoral region of each baboon, using heparinized 3-ml syringes, prior to antibiotic administration and at 15, 30, 60, 120, 240, 360 and 480 minutes after antibiotic administration. The withdrawn samples were centrifuged at 12,000 rpm for one minute and bioassayed by the previously described Bioassay of Plasma Samples method. The results were as follows:

TABLE 2

Antibiotic Bioavailability and Cmax Range in Baboons After Rectal Administration

| Antibiotic | With Absorption Enhancer System | | Control No Absorption Enhancer System | |
|---|---|---|---|---|
| | % Bioavailability | Cmax Range mcg/ml | % Bioavailability | Cmax Range mcg/ml |
| Ceftriaxone | 31.5 ± 13.1 | 18.2–49.6 | 4.3 ± 2.8 | 0.3–9.0 |
| Cefamandole | 46.5 ± 16.6 | 5.9–16.4 | 6.0 ± 2.3 | 2.3–4.6 |
| Cefoxitin | 77.0 ± 22.5 | 4.7–10.8 | 0 | 0 |
| Penicillin G | 38.2 ± 26.1 | 2.0–11.1 | 17.4 ± 8.0 | 1.2–2.4 |

Absorption was also evaluated using a formulation composed of 600 mg of ceftriaxone sodium salt, 200 mg of sodium caprylate, 125 mg of Laureth-12 and 1075 mg of Witepsol H15 (total: 2000 mg). The Bioavailability was 49.3±13.7% and the Cmax range was 68.1–102.8 mcg/ml, compared to 4.3% Bioavailability and 0.3–9.0 mcg/ml Cmax range for the control (600 mg of ceftriaxone sodium salt in suppository vehicle with no absorption enhancers).

By way of illustration, some suitable formulations for various dosage forms in accordance with this invention are set forth below. While ceftriaxone, the preferred antibiotic for this invention, is used to illustrate these formulations, it should be understood that other antibiotics may be substituted in appropriate amounts.

ORAL DOSAGE FORMS

| | | per capsule | | | |
|---|---|---|---|---|---|
| A) | Ceftriaxone (sodium) | 60 mg | 120 mg | 210 mg | 300 mg |
| | Labrasol | 225 mg | 225 mg | 225 mg | 225 mg |
| | Laureth-12 | 75 mg | 75 mg | 75 mg | 75 mg |
| | Witepsol H15 | 340 mg | 340 mg | 340 mg | 340 mg |
| B) | Ceftriaxone (sodium) | 60 mg | 120 mg | 210 mg | 300 mg |
| | Sodium caprylate | 200 mg | 200 mg | 200 mg | 200 mg |
| | Laureth-12 | 75 mg | 75 mg | 75 mg | 75 mg |
| | Witepsol H15 | 365 mg | 365 mg | 365 mg | 365 mg |
| C) | Ceftriaxone (sodium) | 60 mg | 120 mg | 210 mg | 300 mg |
| | Acconon Con | 225 mg | 225 mg | 225 mg | 225 mg |
| | Laureth-12 | 75 mg | 75 mg | 75 mg | 75 mg |
| | Witepsol H15 | 340 mg | 340 mg | 340 mg | 340 mg |
| D) | Ceftriaxone (sodium) | 60 mg | 120 mg | 210 mg | 300 mg |
| | Softigen 767 | 225 mg | 225 mg | 225 mg | 225 mg |
| | Laureth-12 | 75 mg | 75 mg | 75 mg | 75 mg |
| | Witepsol H15 | 340 mg | 340 mg | 340 mg | 340 mg |

RECTAL DOSAGE FORMS

-continued

|   | | per suppository | | | |
|---|---|---|---|---|---|
| A) | Ceftriaxone (sodium) | 180 mg | 300 mg | 600 mg | 1200 mg |
|   | Labrasol | 250 mg | 250 mg | 250 mg | 500 mg |
|   | Laureth-12 | 125 mg | 125 mg | 125 mg | 250 mg |
|   | Witepsol H15 | 1445 mg | 1325 mg | 1025 mg | 2050 mg |
| B) | Ceftriaxone (sodium) | 180 mg | 300 mg | 600 mg | 1200 mg |
|   | Sodium caprylate | 200 mg | 200 mg | 200 mg | 400 mg |
|   | Laureth-12 | 125 mg | 125 mg | 125 mg | 250 mg |
|   | Witepsol H15 | 1495 mg | 1375 mg | 1075 mg | 2150 mg |
| C) | Ceftriaxone (sodium) | 180 mg | 300 mg | 600 mg | 1200 mg |
|   | Acconon Con | 250 mg | 250 mg | 250 mg | 500 mg |
|   | Laureth-12 | 125 mg | 125 mg | 125 mg | 250 mg |
|   | Witepsol H15 | 1445 mg | 1325 mg | 1025 mg | 2050 mg |
| D) | Ceftriaxone (sodium) | 180 mg | 300 mg | 600 mg | 1200 mg |
|   | Softigen 767 | 250 mg | 250 mg | 250 mg | 500 mg |
|   | Laureth-12 | 125 mg | 125 mg | 125 mg | 250 mg |
|   | Witepsol H15 | 1445 mg | 1325 mg | 1025 mg | 2050 mg |

The above dosage forms can be prepared as follows:

PROCEDURES

Oral

The base (Witepsol H15) is warmed to 55° C. and the absorption enhancer system components are added to the melt with mixing. The melt is then cooled to 45° C. and the drug (ceftriaxone sodium) is added to the molten mass and mixed until uniformly distributed and free of any aggregates. The mass is homogenized, if necessary, to obtain a uniform suspension. The suspension is filled into gelatin capsules, sealed if necessary, and the capsules are enteric coated.

Rectal

The base (Witepsol H15) is warmed to 55° C. and the absorption enhancer system components are added to the melt with mixing. The melt is then cooled to 45° C. and the drug (ceftriaxone sodium) is added to the molten mass and mixed until uniformly distributed and free of any aggregates. The mass is homogenized, if necessary, to obtain a uniform suspension. The suspension is then filled into suppository shells and allowed to cool and congeal.

We claim:

1. A method for treating a bacterial infection in a mammal, comprising orally administering to the mammal a therapeutic amount of a pharmaceutical composition comprising:
   (a) a cephalosporin; and
   (b) an absorption enhancing amount of a two-component absorption enhancing system including:
      (1) a compound of the formula:

$CH_3(CH_2)_{10}CH_2(OCH_2CH_2)_nOH$ wherein n has an average value of 12; and
   (2) a pharmaceutically acceptable salt of caprylic acid, wherein the weight ratio of component (b)(1) to component (b)(2) is from about 1:10 to about 10:1;
   said composition being coated with a pharmaceutically acceptable enteric coating material.

2. The method according to claim 1, in which component (b)(2) is an alkali metal or alkaline earth metal salt of caprylic acid.

3. The method of claim 2, wherein component (b)(2) is sodium caprylate, potassium caprylate, or calcium caprylate.

4. The method of claim 3, wherein component (b)(2) is sodium caprylate.

5. The method according to claim 1, in which the cephalosporin is ceftriaxone or a pharmaceutically acceptable salt, ester, or hydrate thereof.

6. The method according to claim 4, in which the cephalosporin is ceftriaxone or a pharmaceutically acceptable salt, ester, or hydrate thereof.

7. The method of claim 1, further comprising adding to the composition a pharmaceutically acceptable carrier suitable for forming a unit dose of the composition for oral administration.

8. The method of claim 6, wherein the pharmaceutically acceptable enteric coating material is polyvinyl acetate phthalate or hydroxypropyl methylcellulose phthalate.

9. The method of claim 1, wherein the weight ratio of component (b)(1) to component (b)(2) is about 1:4 to about 4:1.

10. The method of claim 8, wherein the weight ratio of component (b)(1) to component (b)(2) is about 1:4 to about 4:1.

11. A solid pharmaceutical unit dose comprising:
   (a) a therapeutic effective amount of a cephalosporin; and
   (b) an absorption enhancing amount of a two-component absorption enhancing system including:
      (1) a compound of the formula:

$CH_3(CH_2)_{10}CH_2(OCH_2CH_2)_nOH$ wherein n has an average value of 12; and
   (2) a pharmaceutically acceptable salt of caprylic acid, wherein the weight ratio of component (b)(1) to component (b)(2) is from about 1:10 to about 10:1;
   said unit dose form being coated with a pharmaceutically acceptable enteric coating material.

12. The pharmaceutical unit dose according to claim 11, in which component (b)(2) is an alkali metal or alkaline earth metal salt of caprylic acid.

13. The pharmaceutical unit dose of claim 12, wherein component (b)(2) is sodium caprylate, potassium caprylate or calcium caprylate.

14. The pharmaceutical unit dose of claim 11, wherein component (b)(2) is sodium caprylate.

15. The pharmaceutical unit dose according to claim 11, in which the cephalosporin is ceftriaxone or a pharmaceutically acceptable salt, ester, or hydrate thereof.

16. The pharmaceutical unit dose according to claim 14, in which the caphalosporin is ceftriaxone or a pharmaceutically acceptable salt, ester, or hydrate thereof.

17. The pharmaceutical unit dose of claim 11, wherein the pharmaceutically acceptable enteric coating material is polyvinyl acetate phthalate or hydroxyprophyl methylcellulose phthalate.

18. The pharmaceutical unit dose of claim 11, wherein the weight ratio of component (b)(1) to component (b)(2) is about 1:4 to about 4:1.

19. The pharmaceutical unit dose of claim 11, wherein the cephalosporin is ceftriaxone or a pharmaceutically acceptable salt, ester, or hydrate thereof; and component (b)(2) is sodium caprylate.

20. The pharmaceutical unit dose of claim 19, wherein the weight ratio of component (b)(1) to component (b)(2) is about 1:4 to about 4:1.

21. The pharmaceutical unit dose of claim 20, wherein the pharmaceutically acceptable enteric coating material is polyvinyl acetate phthalate or hydropropyl methylcellulose phthalate.

* * * * *